Figure 1:
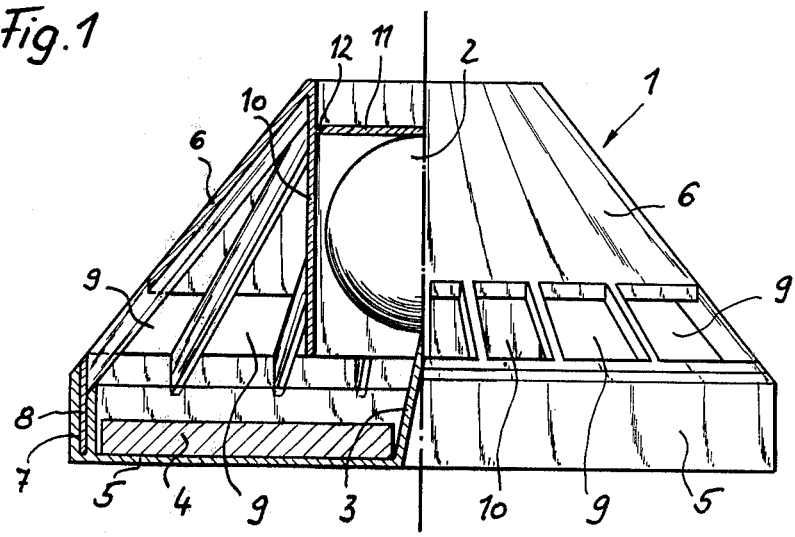

United States Patent [19]

Schimanski et al.

[11] 4,247,042
[45] Jan. 27, 1981

[54] VAPORIZER FOR INSECTICIDES AND/OR OTHER VOLATILE ACTIVE SUBSTANCES

[75] Inventors: Georg Schimanski, Breckerfeld; Fritz von Philipp, Neuburg, both of Fed. Rep. of Germany

[73] Assignee: Globol-Werk GmbH, Fed. Rep. of Germany

[21] Appl. No.: 12,441

[22] Filed: Feb. 15, 1979

[30] Foreign Application Priority Data

Feb. 22, 1978 [DE] Fed. Rep. of Germany ....... 2807424

[51] Int. Cl.³ .............................................. B05B 17/00
[52] U.S. Cl. ...................................... 239/43; 239/47; 239/59
[58] Field of Search ................... 222/5, 80, 82, 83, 90; 239/43, 56, 57, 59, 34, 309, 47, 58

[56] References Cited

U.S. PATENT DOCUMENTS

| 2,219,959 | 10/1940 | Laidley | 239/43 |
| 2,642,310 | 6/1953 | Mack et al. | 239/59 X |
| 3,538,866 | 11/1970 | Gaines | 239/309 X |
| 3,727,840 | 4/1973 | Nigro | 239/43 |

Primary Examiner—Robert B. Reeves
Assistant Examiner—Gene A. Church
Attorney, Agent, or Firm—Jacobs & Jacobs

[57] ABSTRACT

A vaporizer for insecticides and other volatile active substances comprising a housing provided with openings and within which housing the active substances are hermetically enclosed. The vaporizer is preferably made of a plastic or other flexible material and may be carried out in various specific embodiments wherein the active substances, which may be toxic, are kept safely out of contact with humans and can be made available for their intended use in controlled and variable amounts. The active substances may be in a spherical or lenticular casing or housing and can be released from outside in a manner to be volatilized for insecticidal or other activity. There is a holder provided for absorption of the volatiles emerging from the casing after the latter is opened by a member actuable externally thereof for cutting the same.

12 Claims, 6 Drawing Figures

VAPORIZER FOR INSECTICIDES AND/OR OTHER VOLATILE ACTIVE SUBSTANCES

In that case, an absorptive plate which contains the active substances is enclosed in a gas-tight casing and the latter is so inserted in a flat container having openings that the end parts of the casing protrude from the container.

In this way while the active substances are hermetically sealed until they are used so that storage for a long time is possible without loss of active substances and furthermore this device can be placed relatively rapidly in operation merely by cutting off the end part of the casing extending out of the container with a pair of scissors and pulling the casing out of the container, nevertheless there is then at least the danger that one will come into contact with the active substances which have deposited on the inside of the opened casing and which are frequently toxic also dangerous to humans in this concentrated form.

It is the object of the invention to create by simple means for a vaporizer of long storage life of the type described above, the possibility of excluding any danger of contact with the active substances. Furthermore, the placing in operation of the device is also to be further simplified. In addition, the delivery of active substances in variable dose is to be possible.

This purpose is achieved in accordance with the invention in the manner that an opener which is screened from the housing, and can be operated from the outside and cut through the casing is provided as well as within the housing, a holder which can absorb active substances coming from the opened casing and has active-substance vaporization surfaces which face the openings of the housing.

By these measures the auxiliary means, such as scissors, heretofore necessary for opening the casing are now dispensed with.

In addition to this, after the casing is opened it remains within the housing, reliably screened off from contact.

In addition, the intensity of the volatilization of the active substance can also be varied by an opening of greater or lesser size in the casing.

It is advantageous if the absorptive holder is arranged on the bottom of the housing and if both the casing which contains the active substances and the opener are arranged above the holder.

One embodiment of the object described above which is of particularly simple form and accordingly also easy to manufacture as well as reliable in operation is characterized by the fact that a punch or the like protrudes upward, as casing opener, from the bottom of the housing while above the punch there is arranged a shaft in which the casing which contains the active substances is inserted, and by the fact that a push member which acts on the casing and can be engaged in the shaft is provided.

One possibly preferred variant of a detail described above is characterized by the fact that a punch or the like which serves as opener is arranged on the push member.

It is also possible to provide an opener both on the bottom of the lower part of the housing and on the push member, said openers being directed opposite each other.

Another development of the above-described object which is favorable from the standpoint of manufacture consists therein that the housing is provided, above the shaft, with a housing wall part which forms the push member, can be bent into the shaft, and acts on the casing.

Preferably, however there is provided on the housing, as push member, a housing-wall part which is defined by intended breaking points, can be broken out, and can be pushed as desired to a greater or lesser depth into the shaft, the push member being preferably furthermore held for frictional displacement in the shaft.

Furthermore it is advantageous if the casing which is filled with active substance has the shape approximately of a ball or of a lens and furthermore preferably consists of resilient material.

In this way it is possible to empty the casing drop by drop by manual action and thus control the volatilization of the active substance.

Furthermore, a development of the above-described object which is favorable from the standpoint of manufacture consists therein that the housing is composed of a shell-like lower part and a hood-shaped upper part which has the openings as well as the shaft, which parts are preferably connected to each other at least by friction.

Another advantageous development of the object described above with which the delivery of the active material can be controlled is characterized by the fact that the housing parts are connected fitted one within the other and have edge parts which are developed so that they can be turned with respect to each other, and that openings are arranged only in these rim parts in such a manner that the openings can be fully or partially closed by turning the housing parts.

In this connection, it is advantageous if detents which secure the interconnection of the housing-parts are provided.

In order also to be able safely to refill the housing, the casing which contains the active substances can be arranged in an axially displaceable container which is open on the bottom and adapted to be inserted in the shaft, the casing being held in the container at least by clamping force.

One preferred further development in this connection is characterized by the fact that on the mouth of the container there are arranged anchorings which positively secure the casing against falling out, preferably in the manner that the mouth of the container is closed by a grid.

Furthermore, one advantageous additional embodiment of the object described above is characterized by the fact that the shaft which receives the casing is arranged on the lower part of the housing, that the upper part of the housing is arranged on the shaft and turnable around it and with respect to the lower part of the housing, and that the inside of the upper part of the housing is developed as a fan.

In this way, the active substance can be delivered by turning the upper part of the housing with respect to the lower part of the housing.

In this connection, it is advantageous for the upper part of the housing to be without openings and to rest in tightly sealing fashion on the lower part of the housing and to be furthermore developed so that it can be lifted off from the lower part of the housing, preferably in the manner that the shaft which receives the casing is arranged vertically adjustable on the lower part of the housing and that the upper part of the housing is supported on the shaft rotatably around same.

In this connection, one preferred development is characterized by the fact that the shaft is provided, at the end thereof facing the lower part of the housing, with a threaded sleeve which is screwed with limited rotation on a threaded pin which protrudes axially from the lower part of the housing, and that ducts are provided which lead, within the wall of the shaft, from the inside of the shaft to the inside of the housing.

In this way it is possible, even with a vaporizer equipped with a manually actuatable fan, continuously to vary the cross section of passage of the housing openings through which the volatile active substances can escape.

Several embodiments of the invention are shown in the drawing and will be described in further detail below.

Figure 2:
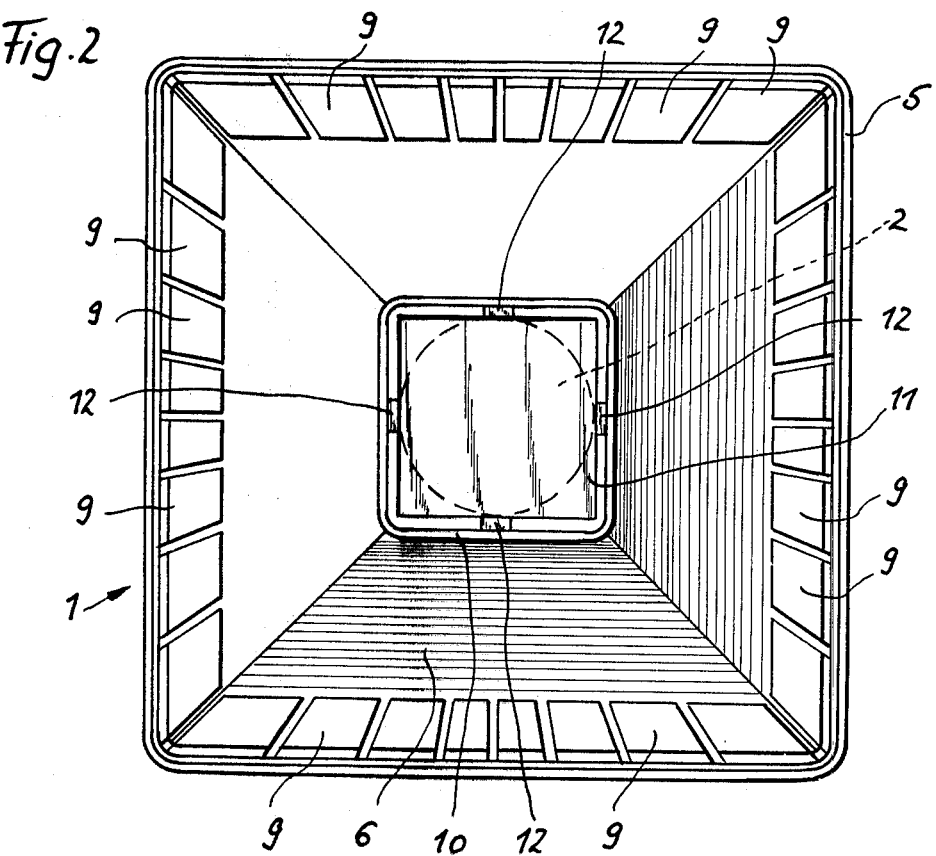
Figure 3:
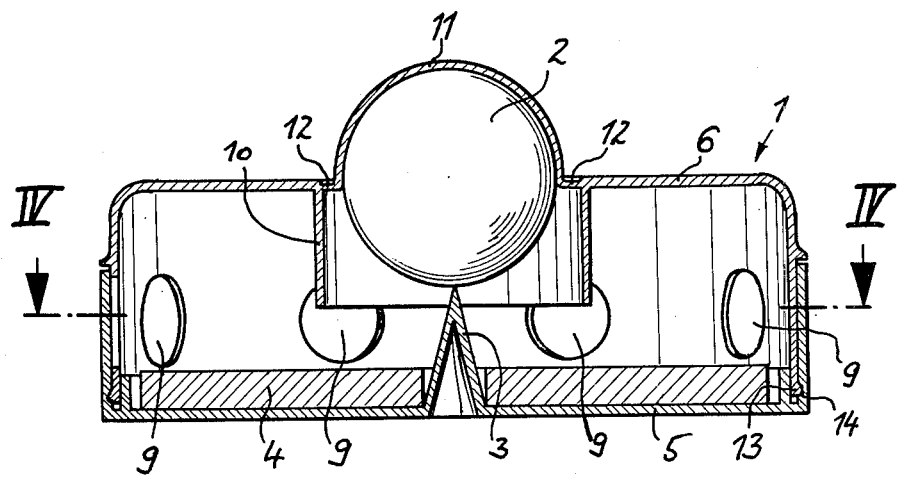
Figure 4:
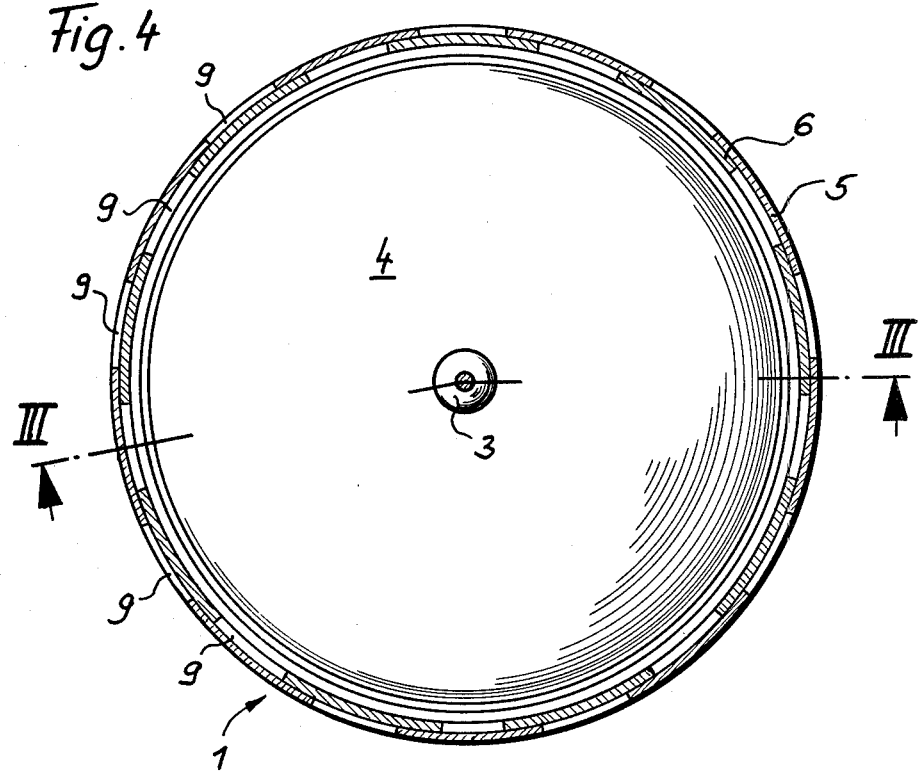
Figure 5:
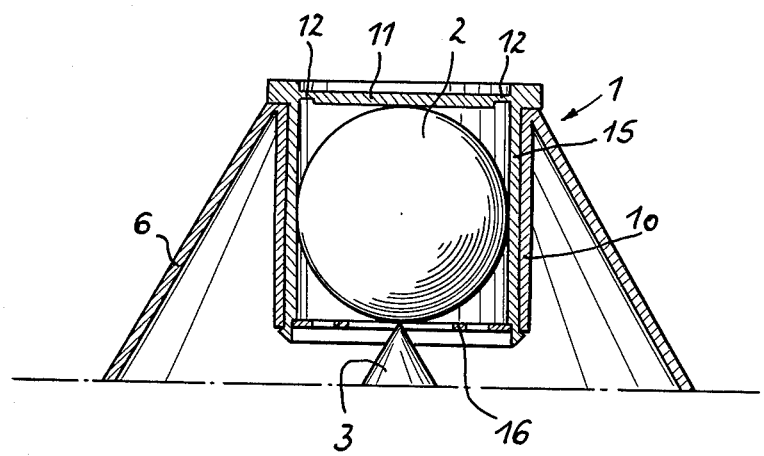
Figure 6:
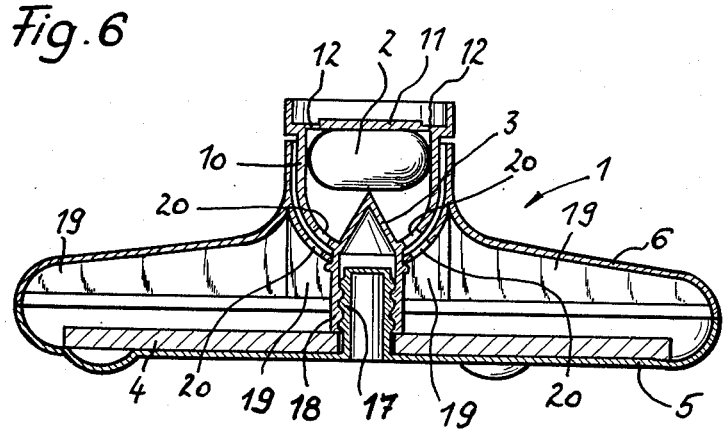

FIG. 1 shows a vaporizer device half in longitudinal section and half in front view, FIG. 2 is a view thereof seen from above, FIG. 3 shows another embodiment along the line III—III of FIG. 4, FIG. 4 shows the same embodiment along the line IV—IV of FIG. 3, FIG. 5 shows a variant detail in longitudinal section, FIG. 6 shows still another embodiment in longitudinal section.

All of the embodiments have a housing 1 of plastic in which there are arranged a casing 2 filled with insecticides and/or other volatile active substances, an opener 3 which is actuatable from the outside and can cut the casing, and a holder 4 which absorbs the active substances emerging from the opened casing 2.

The housings are in each case formed of a shell-like housing lower part 5 and a hood-like housing upper part 6.

In FIGS. 1 and 2 there is formed on the lower part 5 a circumferential, upwardly open groove 7 into which there frictionally engages an edge part 8 developed on the upper part 6 and corresponding in shape to said groove.

On the upper part 6 having the openings 9 there is formed a shaft 10 into which the casing 2 is inserted. Opposite the shaft 10, which is open on its bottom, a punch is developed on the lower part 5 it forming the opener 3.

At its top the shaft 10 is closed by a push member 11 developed thereon which acts on the casing 2. The push member is surrounded by predetermined breaking points 12.

In order to operate this vaporizer it is merely necessary to push the push member 11 into the shaft 10, whereby the push member 11 breaks off from the shaft 10 and presses the casing 2 against the punch-shaped opener 3 which cuts the casing 2 so that the active substances can emerge from the casing 2 and be absorbed by the disk-shaped holder 4 which is held on the bottom of the housing, covering its entire surface, and can evaporate there.

Longitudinally extending ribs (now shown) can be developed in the shaft 10, distributed on its periphery, on which ribs the push member 11 which has been broken off is supported by friction so that the shaft 10 remains closed at the top even after the breaking off of the push member 11.

It is also possible to force the active substances out of the casing 2 by means of the push member 11.

In the embodiment shown in FIGS. 3 and 4, both the lower part 5 and the upper part 6 of the housing are of circular cross section and they are connected in rotatable manner with each other.

In order that the upper part 6 cannot unintentionally come loose from the bottom part 5, a rib 13 is developed on the upper part 6 and a notch 14 on the lower part.

In the overlapping edge portions of the housing parts 5 and 6 there are provided openings 9 which can be aligned with each other.

Furthermore, in this case, in contradistinction to the device shown in FIGS. 1 and 2, the push member 11 is developed in the shape of a hemisphere which positively grasps the closed casing 2 over about one half of its surface.

In FIG. 5 a pot-shaped container 15 is inserted into the shaft 10 which is developed on the upper part 6 of the housing and is open both on top and on bottom, the casing 2 being inserted in said container. In order that the casing 2 cannot come loose from the container 15, the mouth of the container is closed by a grid 16 which can be passed through by the opener 3.

FIG. 6 shows a vaporizer device having the shape, in cross section, of a circular ring, the upper part 6 of the housing being developed so that it can be lifted off from the bottom part 5 of the housing so as to form a housing opening.

For this purpose, a threaded pin 17 extends axially from the lower part 5 of the housing. On said pin there is screwed a threaded sleeve 18. The latter is developed on the lower end of the shaft 10. On the latter there is rotatably supported the upper part 6 of the housing on which a plurality of radially directed fan blades 19 are formed.

Furthermore, in this case the opener 3 is developed on the shaft 10. Alongside the punch-shaped opener 3 a plurality of ducts 20 are provided distributed over the periphery, through which the active substances emerging from the casing 2 can arrive at the holder 4.

If in the case of this vaporizer, the upper part 6 of the housing is lifted off from the lower part 5 of the housing, the delivery of active substance can be accelerated by turning the upper part 6 of the housing relative to the lower part 5.

All new individual and combination features disclosed in the specification and/or drawing are deemed essential to the invention.

The housing 1 is of plastic material for instance polyethylene. The holder 4 is for instance of cellulose. The casing 2 is for instance gelatin. As insecticides may be used DDVP in liquid form (Dichlorvos).

As other volatile substances there are possible for instance etheral oil in liquid form or synthetical odoriferous substances and perfumes.

What is claimed is:

1. A vaporizer for volatile active substances comprising a casing containing volatile active substances therein, a housing preferably of plastic for the casing and having an upper portion and a lower portion, an absorptive holder in the lower portion of the housing and arranged to absorb volatiles released from the casing, an opener projecting from the holder and supporting the casing, a hollow shaft formed in and as a part of the housing and enclosing the casing, a pushing member above and resting on the casing and attached to the shaft and which, when pushed down into the shaft breaks away from the shaft and acts to depress the casing and causes the opener to pierce the casing, thereby releasing the contents of the casing for absorption by the holder.

2. A vaporizer according to claim 1 wherein the housing has a shell-like lower part on which the absorptive holder rests.

3. A vaporizer according to claim 2 wherein the opener is formed as an upward projection of the shell-like lower part of the casing.

4. A vaporizer according to claim 1 wherein the upper and lower housing portion are frictionally engaged, the casing being in the upper portion and the holder and opener being in the lower portion.

5. A vaporizer according to claim 4 wherein the holder is disk-shaped and covers substantially the entire bottom of the housing.

6. A vaporizer according to claim 1 wherein the pushing member is frictionally held in the shaft.

7. A vaporizer according to claim 1 wherein the lower portion of the housing has an upstanding grooved peripheral member in the groove of which is a frictionally engaged groovefilling element.

8. A vaporizer according to claim 1 wherein the pushing member is of hemispherical shape and the upper and lower portions of the housing are rib-and-motch connected.

9. A vaporizer according to claim 8 wherein the upper portion of the housing is provided with ventilating openings.

10. A vaporizer according to claim 9 wherein the upper portion of the housing is imperforate.

11. A vaporizer according to claim 1 wherein means is provided for normally maintaining the casing in fixed stationary position.

12. A vaporizer according to claim 6 wherein the hollow shaft is vertically adjustable with respect to the lower portion of the housing.

* * * * *